(12) United States Patent
Cantor et al.

(10) Patent No.: US 8,304,194 B2
(45) Date of Patent: *Nov. 6, 2012

(54) QUANTIFICATION OF GENE EXPRESSION

(75) Inventors: Charles R. Cantor, Del Mar, CA (US); Chunming Ding, Singapore (SG)

(73) Assignee: The Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/223,923

(22) Filed: Sep. 1, 2011

(65) Prior Publication Data

US 2012/0028838 A1      Feb. 2, 2012

Related U.S. Application Data

(63) Continuation of application No. 10/655,762, filed on Sep. 5, 2003, now Pat. No. 8,034,567.

(60) Provisional application No. 60/408,819, filed on Sep. 6, 2002, provisional application No. 60/422,030, filed on Oct. 29, 2002.

(51) Int. Cl.
*C12Q 1/68* (2006.01)
*C12P 19/34* (2006.01)

(52) U.S. Cl. ................. 435/6.12; 435/6.1; 435/6.11

(58) Field of Classification Search .................. None
See application file for complete search history.

(56) References Cited

U.S. PATENT DOCUMENTS

| | | | |
|---|---|---|---|
| 5,213,961 | A | 5/1993 | Bunn et al. |
| 5,747,246 | A | 5/1998 | Pannetier et al. |
| 5,906,744 | A | 5/1999 | Carroll et al. |
| 6,013,431 | A | 1/2000 | Soderlund et al. |
| 6,268,147 | B1 | 7/2001 | Beattie et al. |
| 6,297,017 | B1 | 10/2001 | Schmidt et al. |
| 6,387,629 | B1 | 5/2002 | Schneider et al. |
| 6,558,902 | B1 | 5/2003 | Hillenkamp |
| 2002/0025532 | A1 | 2/2002 | Huang |
| 2004/0009495 | A1 | 1/2004 | O'Malley et al. |

FOREIGN PATENT DOCUMENTS

| | | |
|---|---|---|
| WO | 0050869 | 8/2000 |
| WO | 0142496 | 6/2001 |
| WO | 0168913 | 9/2001 |
| WO | 0190399 | 11/2001 |
| WO | 0196607 | 12/2001 |

OTHER PUBLICATIONS

Braun et al., "Improved Analysis of Microsatellites Using Mass Spectrometry." Genomics 46:18-23, 1997.
Buchanan, F. C. et al., "Association of a missense mutation in the bovine leptin gene with carcass fat content and leptin MRNA levels." Genetics Selection Evolution 34(1):105-116, 2002.
Becker et al, Nucleic Acids Research, 17 (22): pp. 9437-9446 (1989).
Ross et al., "Quantitative Approach to Single-Nucleotide Polymorphism Analysis Using MALDI-TOF Mass Spectrometry," BioTechniques, vol. 29, No. 3, pp. 620-629, 2000.
Amexis et al., PNAS, vol. 98, No. 21, pp. 12097-12102, 2001.
Amexis et al, Virology 300(2): pp. 171-179, 2002.
Graber et al., Genetic Analysis Biomolecular Engineering 14: pp. 215-219, 1999.
Matyas et al., Human Mutation 19: pp. 58-68, 2002.
Tang et al., International Journal of Mass Spectrometry, 226: pp. 37-54, 2003.
Wada, Y., Journal of Mass Spectrometry 33: pp. 187-192, 1998.

*Primary Examiner* — Young J Kim
(74) *Attorney, Agent, or Firm* — Nixon Peabody LLP; Ronald I. Eisenstein; Leena H. Karttunen Contarino

(57) ABSTRACT

The present invention relates to a method for measuring the amount of a target nucleic acid in a sample using a standard which is designed to have one base difference compared with the gene of interest or a "target nucleic acid sequence." Use of such standard in combination with a method of "enhancing" the difference in the standard and the test nucleic acid sample using, for example, a base extension reaction carried right at the mutation site allowing amplification of the standard and target nucleic acids with the same efficiency and facilitating quantification of the target nucleic acid. Thereafter a means of quantifying the "enhanced" standard and target nucleic acid samples is used to determine the amount of the target nucleic acid. In the preferred embodiment, the quantification means is Mass Spectrometry.

3 Claims, 8 Drawing Sheets

QUANTIFICATION OF GENE EXPRESSION

CROSS REFERENCE TO RELATED APPLICATIONS

This application is a continuation of U.S. Ser. No. 10/655,762 filed on Sep. 5, 2003, issued as U.S. Pat. No. 8,034,567, which claims the benefit of U.S. Provisional Application No. 60/408,819, filed Sep. 6, 2002, and U.S. Provisional Application No. 60/422,030, filed Oct. 29, 2002 under 35 U.S.C. §119(e) which are herein incorporated by reference in their entirety.

BACKGROUND OF THE INVENTION

Detection and quantification of differentially expressed genes in a number of pathological conditions such as different benign and malignant tumors, neurological disorders, heart disease and autoimmune disorders, would be useful in the diagnosis, prognosis and treatment of these pathological conditions. Quantification of gene expression would also be useful in diagnosis of infectious diseases and following up effects of pharmaceuticals or toxins on molecular level. For example, gene expression data could be used to determine the pharmacological mechanism of a drug or a toxin (Libutti et al., Microarray technology and gene expression analysis for the study of angiogenesis. Expert Opin Biol Ther. 2002 June; 2(5):545-56).

The methods for transcript detection and quantification have traditionally included Northern-blot hybridization, ribonuclease protection assay, and reverse transcriptase polymerase chain reaction (RT-PCR) based methods. However, in addition to suffering from lack of sensitivity (except RT-PCR), these methods are only useful for roughly estimating the relative expression changes of each transcript among samples from different sources. The different RT-PCR based techniques are the most suitable quantification method for diagnostic purposes, because they are very sensitive and thus require only a small sample size which is desirable for a diagnostic test.

Absolute quantification of transcript copy numbers in a sample is a requirement if one wishes to compare gene expression between samples and even within the same sample. However, quantification of nucleic acid copy numbers is difficult using PCR based methods because of the inherent non-linear nature of the PCR reaction. PCR amplification will change from an exponential phase to a plateau phase with the consumption of reagents or enzyme inactivation. Often, the exponential phase of the PCR must be determined separately which may involve sampling of the PCR reactions at different time points or performing the PCR using different dilutions of the template. Further, because of differences in amplification efficiency between templates, the starting quantities of different PCR products cannot be compared directly even in the linear range. Detection of PCR products has traditionally been performed after amplification is completed. Typically, an aliquot of the PCR reaction product is size separated by agarose gel electrophoresis, stained with ethidium bromide, and visualized with ultraviolet light. Alternatively, the primers may be labeled with a fluorescent dye or a radioactive molecule. Comparison of band intensities between samples allows one to qualitatively estimate the relative starting concentrations of templates amplified, but this method is not quantitative and does not result in determination of the absolute copy number.

A number of quantitative RT-PCR based methods have been described including RNA quantification using PCR and complementary DNA (cDNA) arrays (Shalon et al., Genome Research 6(7):639-45, 1996; Bernard et al., Nucleic Acids Research 24(8):1435-42, 1996), solid-phase mini-sequencing technique, which is based upon a primer extension reaction (U.S. Pat. No. 6,013,431, Suomalainen et al. Mol. Biotechnol. June; 15(2):123-31, 2000), ion-pair high-performance liquid chromatography (Doris et al. J. Chromatogr. A May 8; 806(1):47-60, 1998), and 5' nuclease assay or real-time RT-PCR (Holland et al. Proc Natl Acad Sci USA 88: 7276-7280, 1991).

It would be useful to develop a method which allows a sensitive and accurate mRNA transcript quantification, can be easily automated and scaled up to accommodate testing of large numbers of sample and overcomes the problems associated with PCR amplification. Such a method would enable diagnosing different pathological conditions, including viruses, bacteria and parasites, as well as different benign and malignant tumors, neurological disorders, heart disease and autoimmune disorders. Such a method would also allow quantifying the transcripts of interest for diagnostic, prognostic and therapeutic purposes, and would ultimately facilitate pharmacogenomic applications. Such a method would also allow screening a large number of agents for effects on gene expression.

SUMMARY OF THE INVENTION

The present invention relates to a method for measuring the amount of a target nucleic acid in a sample using a standard which is designed to have one base difference compared with the gene of interest or a "target nucleic acid sequence." Use of such standard in combination with a method of "enhancing" the difference in the standard and the test nucleic acid sample using, for example, a base extension reaction carried right at the mutation site allowing amplification of the standard and target nucleic acids with the same efficiency and facilitating quantification of the target nucleic acid. Thereafter a means of quantifying the "enhanced" standard and target nucleic acid samples is used to determine the amount of the target nucleic acid. In the preferred embodiment, the quantification means is Mass Spectrometry.

The method of the present invention is sensitive, accurate and highly reproducible and it is also independent of PCR cycle number, which greatly simplifies the analysis. The method of the present invention is unique because different alleles of the same gene can be measured simultaneously, absolute quantification of gene expression can be achieved so that the data can be directly compared from different experiments, and it can be applied in high-throughput analysis and virtually no optimization is needed for PCR. Additionally, the method allows for accurate determination of copy number of infectious agents such as viruses, bacteria and parasites in a biological specimen such as human fluids (serum, plasma, etc).

The invention provides a method of quantifying the amount of a target gene/nucleic acid or a plurality of target genes/nucleic acids in a biological specimen comprising adding a known concentration of a nucleic acid standard to the biological specimen, wherein the standard is designed to have one base difference with the target nucleic acid sequence; amplifying a sample with the target and standard nucleic acids, for example, using a polymerase chain reaction, removing the excessive dNTPs, for example by treating the amplified sample with a phosphatase (e.g. Shrimp alkaline phosphatase), and consequently enhancing the nucleic acid difference between the standard and the test nucleic acid, for example, by extending the differing base in the target and the standard nucleic acid samples. The standard and the target nucleic acid produce two different products, typically having one to two bases difference, and are subsequently quantified. The concentration of a transcript can be calculated based upon the amount of standard present in the amplified sample.

Fore example, this invention enables detection, and more importantly, quantification of infectious agents. It can easily be used in a high throughput way where around 100 infectious agents can be quantified on a 384-format silicon chip.

In one preferred embodiment, the quantification is performed based upon the different mass of the "enhanced" target and standard nucleic acid products using MALDI-TOF mass spectrometry (e.g., Using Sequenom's MassArray™ system), wherein the ratio of the peaks in the mass spectrum is used to calculate the ratio of the standard and the target nucleic acid. The concentration of a transcript can be calculated based upon the initial amount of standard used/added in the sample before amplification.

In one preferred embodiment, the enhancement of the nucleic acid difference between the standard and the target nucleic acid is performed using primer extension methods.

In another embodiment, the enhancement of the nucleic acid difference in the target and the standard after the PCR is performed using fluorescence tagged dNTP/ddNTP for base extension.

In yet another embodiment, the enhancement of the nucleic acid difference in the target and the standard after the PCR is performed using different dye-labeled ddNTPs which are differentially incorporated into the target and standard nucleic acids in a primer extension reaction.

In one embodiment, the enhancement of the nucleic acid difference in the target and the standard after the PCR, is performed using real time PCR.

In another embodiment, the enhancement of the nucleic acid difference in the target and the standard after the PCR is performed using hybridization based techniques wherein two oligonucleotides specific for either the target or the standard are designed for hybridization.

In another embodiment, the enhancement of the nucleic acid difference in the target and the standard after the PCR is performed using pyrosequencing technology.

In another embodiment, the enhancement of the nucleic acid difference in the target and the standard after the PCR is performed using a third wave invader assay using an artificial single nucleotide polymorphism (SNP) as an internal reference. In an alternative embodiment, when using pyrosequencing, no pre-amplification is needed.

In one embodiment, the target nucleic acid is a nucleic acid from at least one infectious agent.

In yet another embodiment, the invention provides a kit comprising at least one preferably several different primers designed to differ by one nucleic acid from at least one, preferably several target nucleic acids, in different vials or preferably, all standard nucleic acids in one vial having a known predetermined concentration in a buffer suitable for a PCR or direct enhancement reactions to enhance the difference between the standard and a corresponding target nucleic acid as described above. The kit also comprises a manual explaining the reaction conditions and the measurement of the amount of target nucleic acid(s) using the standard nucleic acid(s). Kits contemplated by the invention include, but are not limited to kits for determining the amount of infectious agents in a biological sample and kits determining the amount of one or more transcripts that is expected to be increased or decreased after administration of a medicament or a drug, or as a result of a disease condition such as cancer.

BRIEF DESCRIPTION OF THE FIGURES

FIG. 3A shows the mass spectrums, and FIG. 3B shows the plot of actual concentration ratio versus the ratio of signal intensity (peak area) in the mass Spectrum.

In FIG. 4A the ratio is 1:1; in FIG. 4B the ratio is 3:1; in FIG. 4C the ratio is 10:1; in FIG. 4D the ratio is 1:3; and in FIG. 4E the ratio is 1:10, but at fixed total concentration ($2*10^{-7}$ µg/µL). The templates were amplified by PCR (30 cycles), base extension (40 cycles), then spotted onto a silicon chip pre-spotted with a matrix of 3-hydroxypicolinic acid (HPA), and analyzed with MALDI-TOF.

DETAILED DESCRIPTION OF THE INVENTION

Figure 1:
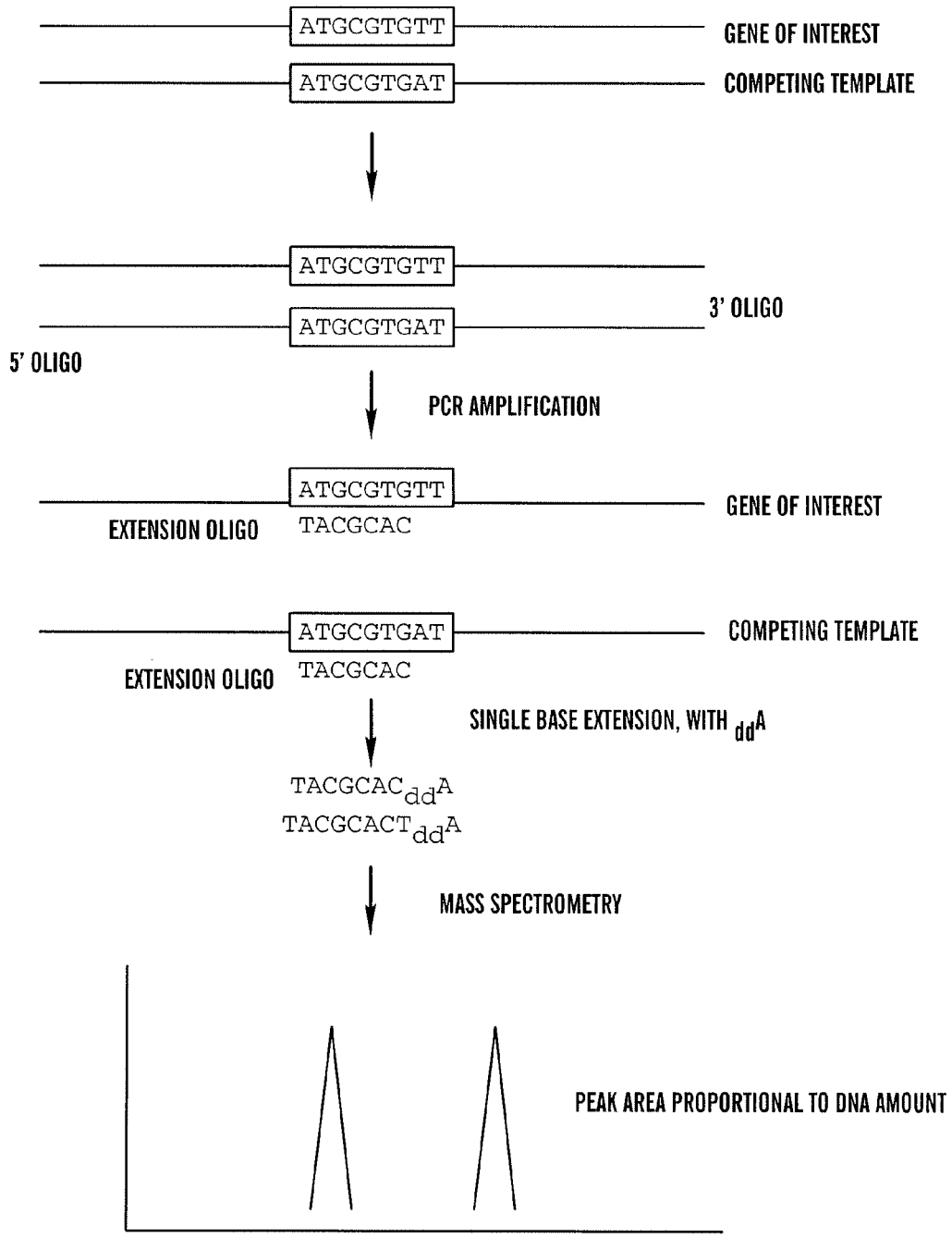
FIG. 1 shows a flow chart of the real competitive PCR and Mass Spectrometry approach for measuring gene expression. For simplicity, only one DNA strand is shown. Also extension oligos are generally around 20 bases, instead of 7 bases shown in the flow chart.

The present invention relates to a novel approach in measuring gene expression or amount of nucleic acid in a sample. This approach combines competitive PCR (polymerase chain reaction), base extension and thereafter measured. The method can be used for directly measuring copy numbers of specific genes, or comparing relative up or down regulations of specific genes from different samples.

A standard nucleic acid (either DNA or RNA) with known concentration is added to the RNA sample (for RNA standard) or the reverse transcription product (for DNA standard). The reverse transcription product including the standard is then amplified by PCR. The standard is designed to have one base mutation difference compared with the gene of interest, i.e. the target nucleic acid. Thus, the standard and the target nucleic acid are amplified with same efficiency in PCR. And these two can be identified, using, for example a base extension reaction carried right at the mutation site.

The amount of the PCR products is consequently measured by any of a variety of means, preferably by Mass Spectrometry (MALDI-TOF, or Matrix Assisted Laser Desorption Ionization—Time of Flight). The peak area ratio between the products from the standard and the gene of interest represents the ratio of the standard and the gene of interest. Since the concentration of the standard is known, the concentration of the gene of interest can be calculated.

The method of the present invention is unique in at least the following aspects. First of all, the natural mutations of genes can be selected to construct standards. Therefore, not only the expression level of the genes can be measured, but also the genotype of the genes expressed can be determined. Second, the usage of a single point mutation in PCR guarantees virtually identical amplification. This eliminates the problems arising from differential amplifications in other competitive PCR approaches where the standards generally are of different lengths with the genes.

In the preferred embodiment, the combination of base extension and MALDI-TOF MS detection also eliminates the problems from heteroduplex formation encountered by traditional detection method such as gel electrophoresis. Also, the extension product from the standard serves as an internal standard in MALDI-TOF MS. Thus, the amount of the nucleic acids can be quantitatively measured when the amount of the standard added to the reaction is known.

This approach has at least the following advantages. First, this method requires little optimization in PCR. Second, this method is not dependent on PCR cycle numbers. Third, the method is highly accurate, sensitive, and reproducible. Fourth, the method can be used to for high throughput gene expression analysis where the expression of at least 50-100, or even up to at least 1000 genes can be measured on one 384-silicon chip.

As shown in the following examples, the analysis of GAPDH, HMBS and CXCR4 expression in human cultured cells by this method produced results consistent with other methods.

As used herein, the term "biological sample" refers to any biological material obtained from any source (e.g. human, animal, plant, bacteria, fungi, protist, virus). For use in the invention, the biological sample should contain a nucleic acid molecule. Examples of appropriate biological samples for use in the instant invention include: solid materials (e.g tissue, cell pellets, biopsies) and biological fluids (e.g. urine, blood, saliva, amniotic fluid, mouth wash). Nucleic acid molecules can be isolated from a particular biological sample using any of a number of procedures, which are well-known in the art, the particular isolation procedure chosen being appropriate for the particular biological sample.

Viruses, bacteria, fungi and other infectious organisms contain distinct nucleic acid sequences, which are different from the sequences contained in the host cell. Detecting or quantifying nucleic acid sequences that are specific to the infectious organism is important for diagnosing or monitoring infection. Examples of disease causing viruses that infect humans and animals and which may be detected by the disclosed processes include: Retroviridae (e.g., human immunodeficiency viruses, such as HIV-1 (also referred to as HTLV-III, LAV or HTLV-III/LAV, See Ratner, L. et al., Nature, Vol. 313, Pp. 227-284 (1985); Wain Hobson, S. et al, Cell, Vol. 40: Pp. 9-17 (1985)); HIV-2 (See Guyader et al., Nature, Vol. 328, Pp. 662-669 (1987); European Patent Publication No. 0 269 520; Chakraborti et al., Nature, Vol. 328, Pp. 543-547 (1987); and European Patent Application No. 0 655 501); and other isolates, such as HIV-LP (International Publication No. WO 94/00562 entitled "A Novel Human Immunodeficiency Virus"; Picornaviridae (e.g., polio viruses, hepatitis A virus, (Gust, I. D., et al., Intervirology, Vol. 20, Pp. 1-7 (1983); entero viruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae, Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatites (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). Examples of infectious bacteria include: *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*.

This technique can be directly applied in developing technologies for high throughput and accurate gene expression analysis. It could also be used to develop clinical diagnosis chips where measurement of at least about 2, 5, 10, 25, 50-100 and up to at least 1000 genes can be used for disease diagnosis.

The method for "enhancing" PCR products wherein the base difference between the standard and the target nucleic acid has been enhanced according to the present invention include, but are not limited to PYROSEQUENCING™, real time PCR, hybridization-based techniques, third wave invader assay, fluorescence-based PCR techniques, solid-phase minisequencing. Quantification of the "enhanced" PCR products can consequently be performed utilizing the mass difference of the target and the standard enhanced nucleic acid product using, for example, MALDI-TOF mass spectrometry (MS).

The term "enhancing" as used in the present invention is intended to cover different techniques whereby the target and the standard nucleic acid are made to include a difference in their mass. Therefore, because the standard and the target nucleic acid have preferably only one base difference, they can be differentiated and the difference amplified or enhanced using, for example a primer extension techniques using labeled nucleic acids. Alternatively, the mass difference can be created using allele-specific hybridization probes or enzymatic cleavage of the different products like in the INVADER assay.

In one embodiment, the PCR products differing by one base pair are enhanced by PYROSEQUENCING™ (Uppsala, Sweden) which is essentially sequencing by synthesis. A sequencing primer, designed directly next to the nucleic acid differing between the target and the standard is first hybridized to a single stranded, PCR amplified, DNA template comprising both the target and the standard PCT product, and incubated with the enzymes, DNA polymerase, ATP sulfurylase, luciferase and apyrase, and the substrates, adenosine 5' phosphosulfate (APS) and luciferin. One of four deoxynucleotide triphosphates (dNTP), for example, corresponding to the nucleotide present in the standard template, is then added to the reaction. DNA polymerase catalyzes the incorporation of the dNTP into the standard DNA strand. Each incorporation event is accompanied by release of pyrophosphate (PPi) in a quantity equimolar to the amount of incorporated nucleotide. Consequently, ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a PYROGRAM™. Each light signal is proportional to the number of nucleotides incorporated and allows determination of the amount of the standard nucleic acid sequence. Thereafter, apyrase, a nucleotide degrading enzyme, continuously degrades unincorporated dNTPs and excess ATP. When degradation is complete, another dNTP is added which corresponds to the dNTP present in the target template the amount of which is to be determined. Finally, addition of dNTPs is performed one at a time. Deoxyadenosine alfa-thio triphosphate (dATPaS) is used as a substitute for the natural deoxyadenosine triphosphate (dATP) since it is efficiently used by the DNA polymerase, but not recognized by the luciferase. Because the amount of the standard added in the PCR is known, the amount of the target can be calculated from the ratio of the incorporated dNTPs. For detailed information about reaction conditions, see, e.g. U.S. Pat. No. 6,210,891, which is herein incorporated by reference in its entirety.

Another example of the methods useful for enhancing the base difference of the standard and the target nucleic acid of PCR products is real time PCR. All real-time PCR systems rely upon the detection and quantitation of a fluorescent reporter, the signal of which increases in direct proportion to the amount of PCR product in a reaction. Examples of real-time PCR method useful according to the present invention include, TaqMan® and molecular beacons, both of which are hybridization probes relying on fluorescence resonance energy transfer (FRET) for quantitation. TaqMan Probes are oligonucleotides that contain a fluorescent dye, typically on the 5' base, and a quenching dye, typically located on the 3' base. When irradiated, the excited fluorescent dye transfers energy to the nearby quenching dye molecule rather than fluorescing, resulting in a nonfluorescent substrate. TaqMan probes are designed to hybridize to an internal region of a PCR product (ABI 7700 (TaqMan™), Applied BioSystems, Foster City, Calif.). Accordingly, two different primers, one hybridizing to the target and the other to the standard nucleic acid template, are designed. The primers are consequently allowed to hybridize to the corresponding nucleic acids in the real time PCR reaction. During PCR, when the polymerase replicates a template on which a TaqMan probe is bound, the 5' exonuclease activity of the polymerase cleaves the probe. Consequently, this separates the fluorescent and quenching dyes and FRET no longer occurs. Fluorescence increases in each cycle, proportional to the rate of probe cleavage.

Molecular beacons also contain fluorescent and quenching dyes, but FRET only occurs when the quenching dye is directly adjacent to the fluorescent dye. Molecular beacons are designed to adopt a hairpin structure while free in solution, bringing the fluorescent dye and quencher in close proximity. Therefore, two different molecular beacons are designed, one recognizing the target and the other the standard nucleic acid. When the molecular beacons hybridize to the target and the standard nucleic acids, the fluorescent dye and quencher are separated, FRET does not occur, and the fluorescent dye emits light upon irradiation. Unlike TaqMan probes, molecular beacons are designed to remain intact during the amplification reaction, and must rebind to target in every cycle for signal measurement. TaqMan probes and molecular beacons allow multiple DNA species to be measured in the same sample (multiplex PCR), since fluorescent dyes with different emission spectra may be attached to the different probes, e.g. different dyes are used in making the standard probe and the target probe. Multiplex PCR allows internal controls to be co-amplified and permits allele discrimination in single-tube, homogeneous assays. (Ambion Inc, Austin, Tex., TechNotes 8(1)-February 2001, Real-time PCR goes prime time).

Yet another method useful for enhancing the difference between the target and standard nucleic acid is the primer extension method as used in the solid-phase mini-sequencing (Hultman, et al., 1988, Nucl. Acid. Res., 17, 4937-4946; Syvanen et al., 1990, Genomics, 8, 684-692). In the original reports, the incorporation of a radiolabeled nucleotide was measured and used for analysis of the three-allelic polymorphism of the human apolipoprotein E gene. The method of detection of the variable nucleotide(s) is based on primer extension and incorporation of detectable nucleoside triphosphates in the detection step. By selecting the detection step primers from the region immediately adjacent to the variable nucleotide, this variation can be detected after incorporation of as few as one nucleoside triphosphate. Labelled nucleoside triphosphates matching the variable nucleotide are added and the incorporation of a label into the detection step primer is measured. The detection step primer is annealed to the copies of the target nucleic acid and a solution containing one or more nucleoside triphosphates including at least one labeled or modified nucleoside triphosphate, is added together with a polymerizing agent in conditions favoring primer extension. Either labeled deoxyribonucleoside triphosphates (dNTPs) or chain terminating dideoxyribonucleoside triphosphates (ddNTPs) can be used, and labels are preferably dyes, including fluorescent dyes. The solid-phase mini-sequencing method is described in detail, for example, in the U.S. Pat. No. 6,013,431 and in Wartiovaara and Syvanen, Quantitative analysis of human DNA sequences by PCR and solid-phase minisequencing. Mol Biotechnol 2000 June; 15(2):123-131.

Another method to enhance the difference in the target and standard nucleic acids in the PCR products is by using fluorescence tagged dNTP/ddNTPs. In addition to use of the fluorescent label in the solid phase mini-sequencing method, a standard nucleic acid sequencing gel can be used to detect the amount of the fluorescent label incorporated into the PCR amplification product. A sequencing primer is designed to anneal next to the base differentiating the standard from the template. A primer extension reaction is performed using chain terminating dideoxyribonucleoside triphosphates (ddNTPs) labeled with a fluorescent dye, one label attached to the ddNTP to be added to the standard nucleic acid and another to the ddNTP to be added to the target nucleic acid. The primer extension products are thereafter separated using a denaturating gel in a fluorescence detecting nucleic acid sequencing machine or using capillary gel electrophoresis and the amount of fluorescent label incorporated to the standard and target nucleic acids results in a fluorescence peak and the amount can be determined from the size of the peak. Standard fluorescent sequencing protocols are known to one skilled in the art (e.g., see Amersham Life Sciences, Uppsala, Sweden, and Applied Biosystems, Foster City, Calif.).

Alternatively, an INVADER® assay can be used (Third Wave Technologies, Inc (Madison, Wis.)). This assay is generally based upon a structure-specific nuclease activity of a variety of enzymes, which are used to cleave a target-dependent cleavage structure, thereby indicating the presence of specific nucleic acid sequences or specific variations thereof in a sample (see, e.g. U.S. Pat. No. 6,458,535). For example, an INVADER® operating system (OS), provides a method for detecting and quantifying DNA and RNA. The INVADER® OS is based on a "perfect match" enzyme-substrate reaction. The INVADER® OS uses proprietary CLEAVASE® enzymes (Third Wave Technologies, Inc (Madison, Wis.)), which recognize and cut only the specific structure formed during the INVADER® process. The INVADER® OS relies on linear amplification of the signal generated by the INVADER® process, rather than on exponential amplification of the target. This allows quantification of target concentration.

In the INVADER® process, two short DNA probes hybridize to the target to form a structure recognized by the CLEAVASE® enzyme. The enzyme then cuts one of the probes to release a short DNA "flap." Each released flap binds to a fluorescently-labeled probe and forms another cleavage structure. When the CLEAVASE® enzyme cuts the labeled probe, the probe emits a detectable fluorescence signal.

The preferred method of quantification is MALDI-TOF MS. Details of the method of quantification using MALDI-TOF MS are given below in the Example.

The invention also envisions a kit comprising at least one preferably several different primers designed to differ by one nucleic acid from at least one, preferably several target nucleic acids, in separate vials or tubes, or preferably, a set of combined standards comprising at least two different standards in the same vial or tube with known amount of dried standard nucleic acid(s) with instructions to dilute the sample in a suitable buffer, such as PBS, to a known concentration for use in the quantification reaction. Alternatively, the standard is pre-diluted at a known concentration in a suitable buffer, such as PBS. Suitable buffer can be either suitable for both for storing nucleic acids and for, e.g., PCR or direct enhancement reactions to enhance the difference between the standard and a corresponding target nucleic acid as described above, or the buffer is just for storing the sample and a separate dilution buffer is provided which is more suitable for the consequent PCR, enhancement and quantification reactions. In a preferred embodiment, all the standard nucleic acids are combined in one tube or vial in a buffer, so that only one standard mix can be added to a nucleic acid sample containing the target nucleic acid.

The kit also preferably comprises a manual explaining the reaction conditions and the measurement of the amount of target nucleic acid(s) using the standard nucleic acid(s) or a mixture of them and gives detailed concentrations of all the standards and of the type of buffer. Kits contemplated by the invention include, but are not limited to kits for determining the amount of infectious agents in a biological sample and kits determining the amount of one or more transcripts that is expected to be increased or decreased after administration of a medicament or a drug, or as a result of a disease condition such as cancer.

EXAMPLE

MALDI-TOF MS is Quantitative

Figure 2:
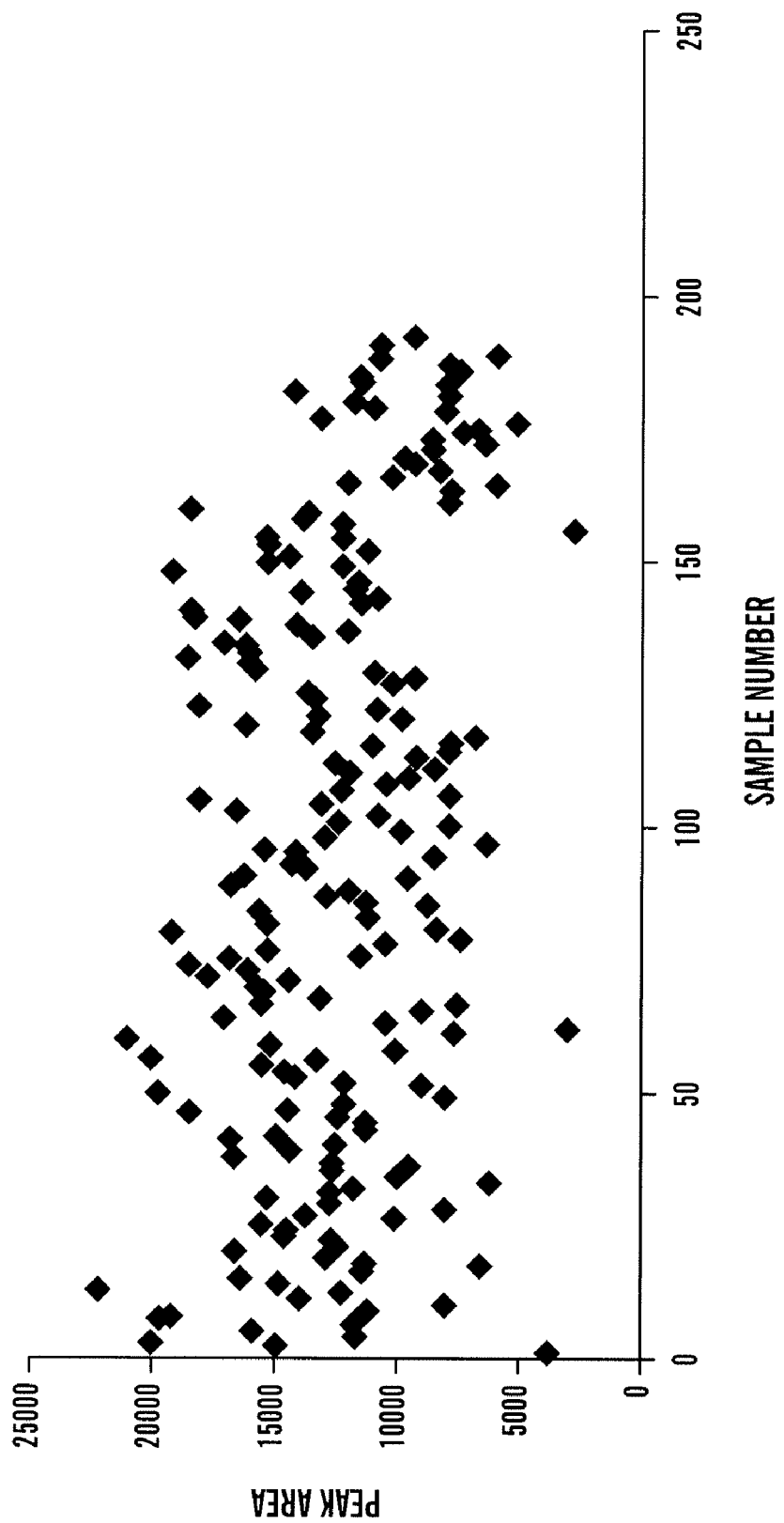
FIG. 2 shows a peak area distribution for the same oligo at the same concentration. Oligo 47954 (5'-ATGGCCACAGT-TGTATCA-3') (SEQ ID NO:1) were used at 0.3 µM and 15 nL is used for spotting onto a silicon chip prespotted with a matrix of 3-hydroxypicolinic acid (HPA). The absolute peak areas for oligos with the same concentration spotted at different positions of the same chip show modest variability with average peak area of 12395 (arbitrary number) and standard deviation of 3737.
Figure 3A:
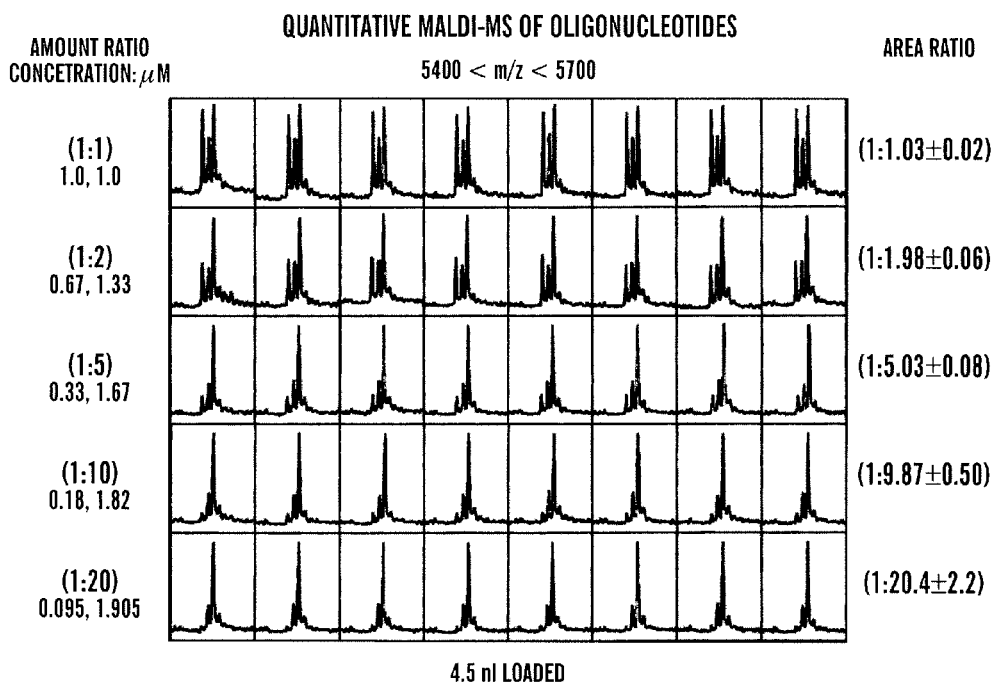
FIGS. 3A AND 3B show peak area ratios in the mass spectrum correlate accurately with oligo concentration ratios. Courtesy of Kai Tang (Sequenom). 4.5 nL of solutions of two oligo mixtures at different ratios (1:1, 1:2, 1:5, 1:10, 1:20) were analyzed using the MassArray™ (Sequenom).
Figure 3B:
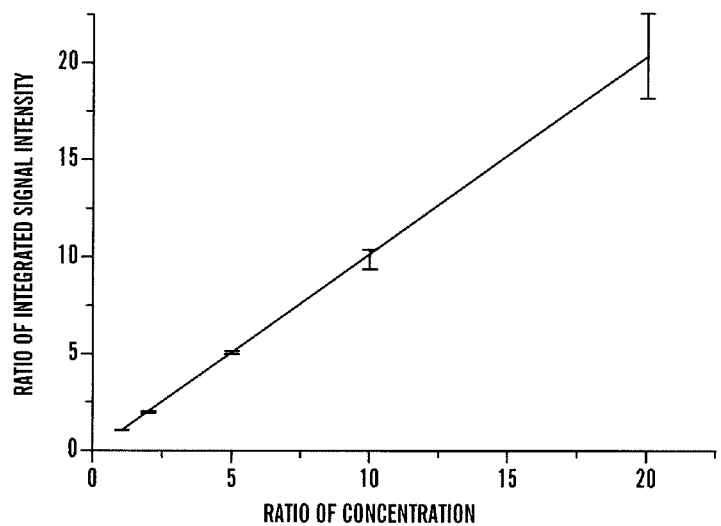
Figure 4B:
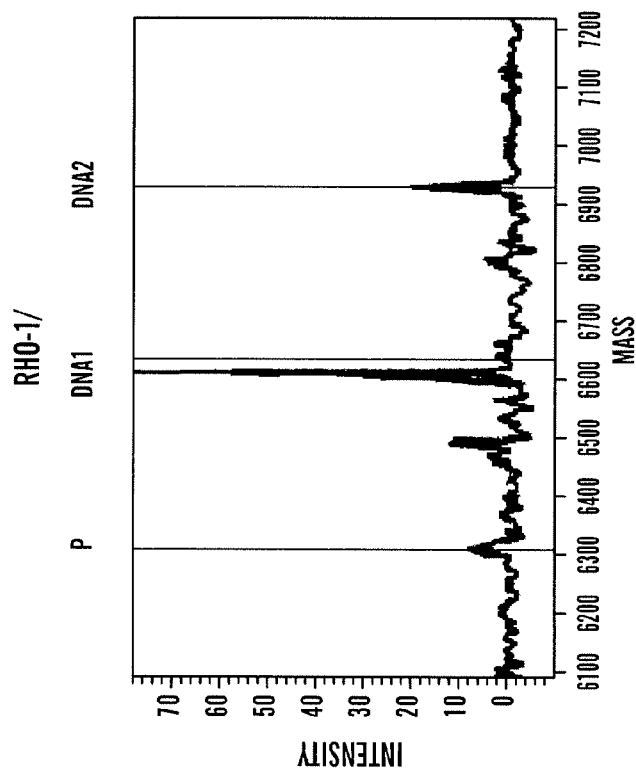
FIGS. 4A-4E show Mass Spectrum for two DNA templates differs only by one base, mixed at different ratios.
Figure 4A:
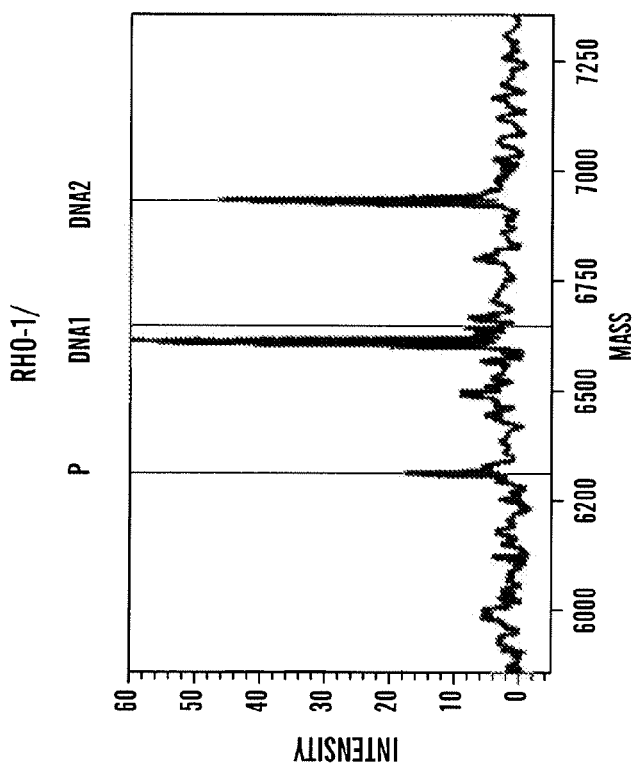
Figure 4D:
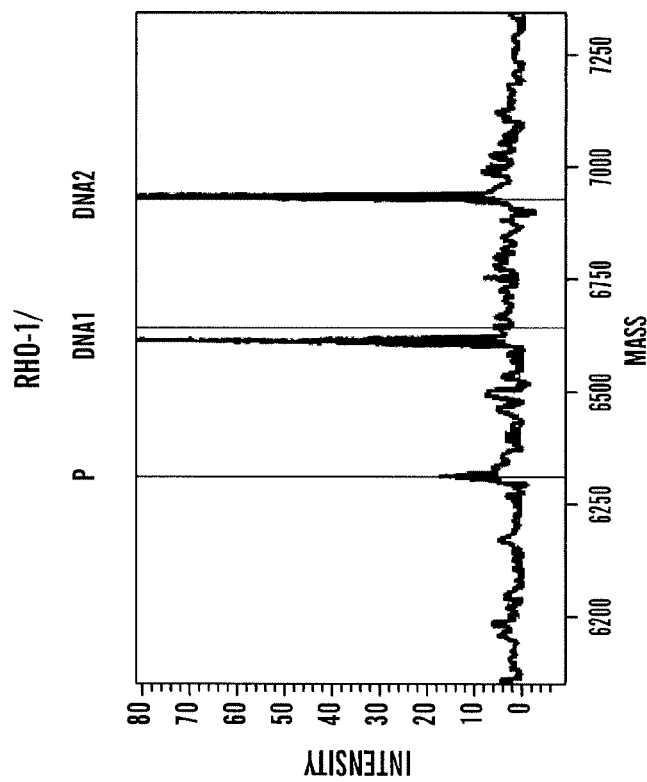
Figure 4C:
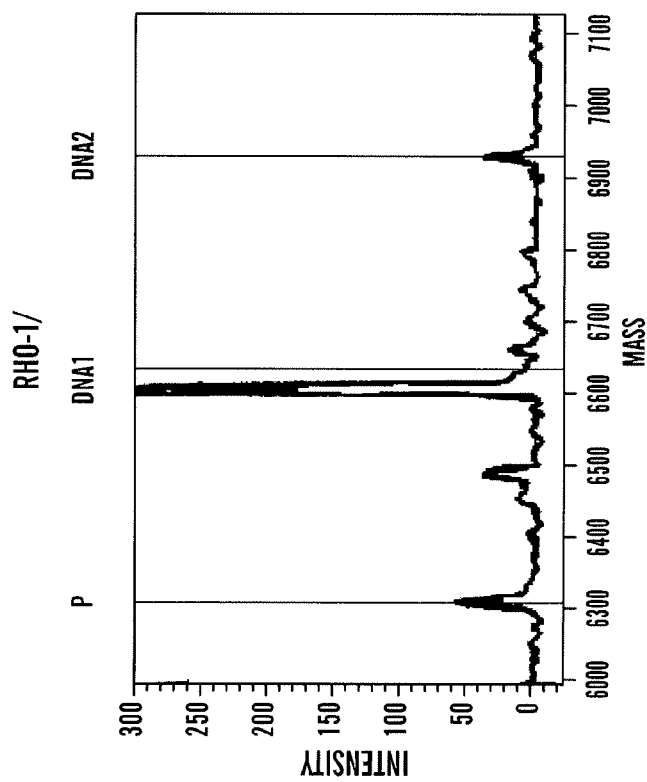
Figure 4E:
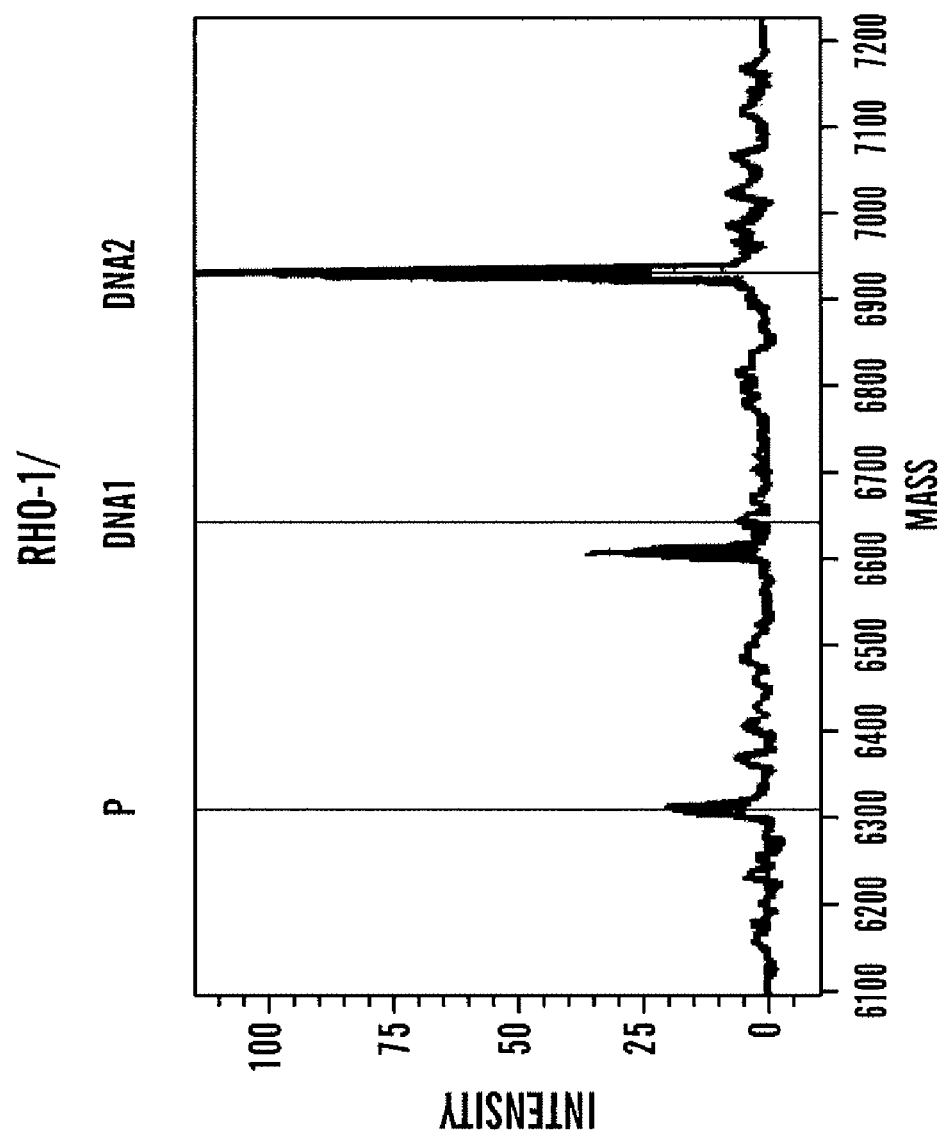

The absolute signals (measured by peak area in the mass spectrum) are relatively consistent in the MALDI-TOF MS experiments in the MassArray system (FIG. 2). This is not good enough for an accurate quantitative analysis. However, by using an oligo with similar sequence as an internal control, we can measure oligo concentration accurately (FIG. 3).

Real Competitive PCR Works in a Two DNA Mixture System, Independent of PCR Cycle Number.

Figure 5:
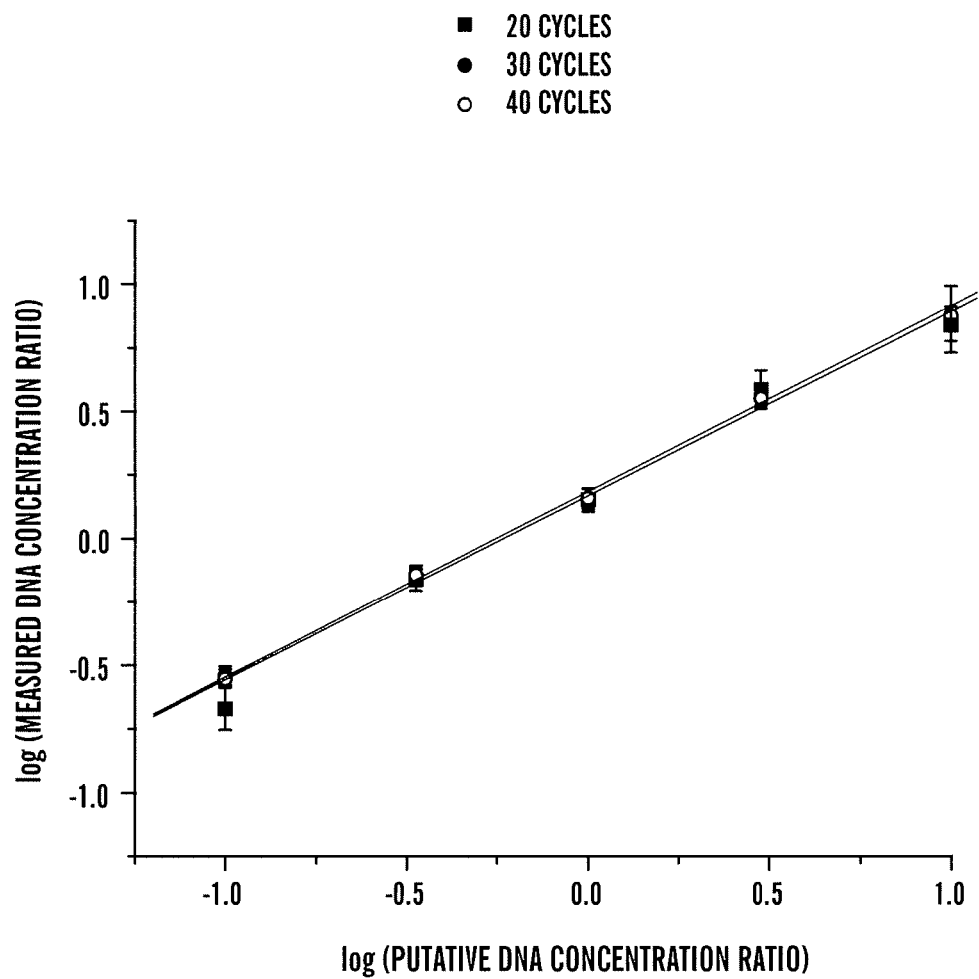
FIG. 5 shows correlations between putative DNA concentration ratios and measured DNA concentration ratios (represented by peak area ratios). PCR amplifications are 20, 30 and 40 cycles respectively and the results are PCR-cycle independent. Each data point is repeated 4 times (n=4) and error bars are shown.
Figure 6:
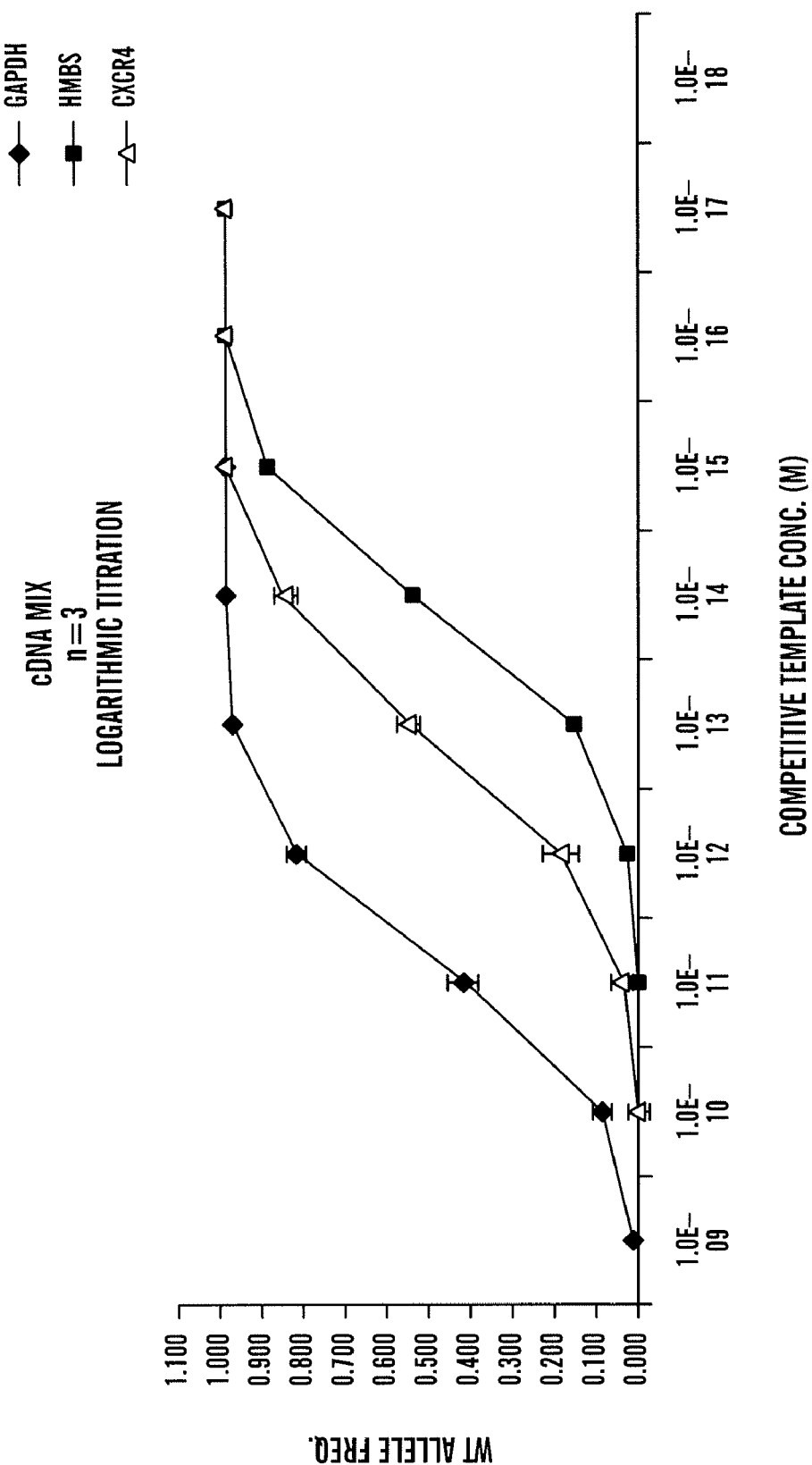
FIG. 6 shows gene expression (GAPDH, HMBS and CXCR4) analysis using real competitive PCR and mass spectrometry.

In this experiment, two DNAs differ only by one nucleotide are mixed at different ratios (10:1, 3:1, 1:1, 1:3, 1:10) with a constant total concentration of $2*10^{-7}$ µg/µL. PCR amplifications with HotStart DNA polymerase were carried out, followed by Shrimp alkaline phosphatase (SAP) treatment to remove excess dNTPs. Then, base extension experiments were carried out with ThermoSequenase with appropriate ddNTP/dNTP mixtures (generally three different ddNTP and one dNTP). The extension products were detected by MALDI-TOF and peak areas were analyzed with the RT (real time) software (Sequenom Inc.). FIG. 4 shows the mass spectrums from template mixtures of five different ratios. FIG. 5 shows the correlations between peak area ratios in mass spectrum and DNA template ratios pre-determined for analysis.

Same experiments were repeated on another pair of two DNAs and similar results as above were obtained. These preliminary data clearly show, at least in this simple artificial system, the real competitive PCR coupled with Mass Spectrometry identification is potentially an accurate way to measure gene expression. The measured peak area ratios correlate linearly ($R^2>0.999$) with the known DNA concentration ratios, up to a 100-fold range. Three gradients at a 100-fold separation of the standard DNA can easily extend the dynamic range to $10^6$, sufficient for most practical applications.

Testing Real Competitive PCR for Human Gene Expression

Expressions of GAPDH, HMBS and CXCR4 in cultured cells were analyzed by this real competitive PCR and MALDI-TOF approach. The competitors for each gene are added individually to the cDNA sample at increasing concentrations. The frequencies of the endogenous genes and their competitors are measured by real competitive PCR and MALDI-TOF MS. Since we know the concentration of the competitors, the expression levels for the genes of interest can be calculated.

Scaling up for High Throughput Gene Expression Analysis

Microarray is an ideal (at least for the moment) method for screening tens of thousands of genes on a small population/condition scale (typically not more than 50). And generally a few hundred genes were chosen by some statistical standard as significantly different between controls and samples. For example, Golub et al. reported using 38 bone marrow samples for microarray analysis and chose 50 genes that collectively were able to distinguish between acute lymphoblastic leukemia (ALL) and acute myeloid leukemia (AML). The large statistical freedom from the small sample size (38 samples) and the large gene number size (6817 genes), together with low accuracy of the microarray method, cast significant doubt on how well this predictor (50 genes) will perform on a larger patient sample size. Economically, it is not feasible to test this with microarray on a patient sample size of hundreds. In our method, we can easily measure about 100 genes expression on a 384 chip and hundreds of patients sample can be tested. Microarray is high throughput gene-number-wise, while our method is high throughput patient-number-wise, which makes these two methods highly complementary.

We can also use this method to study gene expression stoichiometry. The scientific assumption here is that genes (or their products, proteins) that work closely as a functional unit will have similar expression levels as well. Mass Spectrometry has been used to analyze protein complexes (Gavin et al., Ho et al.). We can analyze mRNA expression of these genes in the same complex and the estimate the stoichiometry of these associations.

Computations

The first issue is PCR oligo design. For other RT-PCR methods such as real time PCR, it will be devastating if the amplifications are non-specific for your gene of interest, because it will result in significant underestimate of the expression level. And what's even worse, non-specific amplification could be sample dependent. In our case, since we always have an internal standard in the same reaction with the gene of interest, this problem should be less severe. With that said, it is still important to avoid non-specific amplifications. Another issue in designing amplification oligos arises from multiplexing PCR. Extra care should be taken to avoid primer-primer interactions.

Computational and statistical techniques can also be applied to analyze the spectra. In MALDI-TOF experiments, five different positions of the same sample spot are shot by the laser beam. And, if we do four repetitions of each sample, we will have 20 data points; sufficient to apply statistical models such as normal distribution to more accurately calculate the peak ratios. Another issue is normalizing. Various housekeeping genes (GAPDH, β-actin, cyclophilin, 18s rRNA) have been used. It might be better to use a combination of these genes for normalization.

REFERENCES

1. Amexis, G., et al., Quantitative mutant analysis of viral quasispecies by chip-based matrix-assisted laser desorption/ionization time-of-flight mass spectrometry. Proc Natl Acad Sci USA, 2001. 98(21): p. 12097-102.
2. Bittner, M., et al., Molecular classification of cutaneous malignant melanoma by gene expression profiling. Nature, 2000. 406(6795): p. 536-40.
3. Cho, R. J., et al., A genome-wide transcriptional analysis of the mitotic cell cycle. Mol Cell, 1998. 2(1): p. 65-73.
4. Freeman, W. M., S. J. Walker, and K. E. Vrana, Quantitative RT-PCR: pitfalls and potential. Biotechniques, 1999. 26(1): p. 112-22, 124-5.
5. Gavin, A. C., et al., Functional organization of the yeast proteome by systematic analysis of protein complexes. Nature, 2002. 415(6868): p. 141-7.
6. Golub, T. R., et al., Molecular classification of cancer: class discovery and class prediction by gene expression monitoring. Science, 1999. 286(5439): p. 531-7.
7. Hayward-Lester, A., P. J. Oefner, and P. A. Doris, Rapid quantification of gene expression by competitive RT-PCR and ion-pair reversed-phase HPLC. Biotechniques, 1996. 20(2): p. 250-7.
8. Ho, Y., et al., Systematic identification of protein complexes in Saccharomyces cerevisiae by mass spectrometry. Nature, 2002. 415(6868): p. 180-3.
9. Hughes, T. R., et al., Functional discovery via a compendium of expression profiles. Cell, 2000. 102(1): p. 109-26.
10. Jurinke, C., et al., Automated genotyping using the DNA MassArray technology. Methods Mol Biol, 2001. 170: p. 103-16.
11. Libutti, S. K. and N. G. Costouros, Microarray technology and gene expression analysis for the study of angiogenesis. Expert Opin Biol Ther, 2002. 2(5): p. 545-56.
12. Livak, K. J., et al., Oligonucleotides with fluorescent dyes at opposite ends provide a quenched probe system useful for detecting PCR product and nucleic acid hybridization. PCR Methods Appl, 1995. 4(6): p. 357-62.
13. Lockhart, D. J., et al., Expression monitoring by hybridization to high-density oligonucleotide arrays. Nat Biotechnol, 1996. 14(13): p. 1675-80.
14. McCulloch, R. K., C. S. Choong, and D. M. Hurley, An evaluation of competitor type and size for use in the determination of mRNA by competitive PCR. PCR Methods Appl, 1995. 4(4): p. 219-26.
15. Prediger, E. A., Detection and quantitation of mRNAs using ribonuclease protection assays. Methods Mol Biol, 2001. 160: p. 495-505.
16. Prediger, E. A., Quantitating mRNAs with relative and competitive RT-PCR. Methods Mol Biol, 2001. 160: p. 49-63.
17. Zhang, J., I. N. Day, and C. D. Byrne, A novel medium throughput quantitative competitive PCR technology to simultaneously measure mRNA levels from multiple genes. Nucleic Acids Res, 2002. 30(5): p. e20.

The references cited herein and throughout the specification are herein incorporated by reference in their entirety.

We claim:

1. A method for quantifying the absolute amount of at least two target nucleic acid molecules in a biological sample, the method comprising the steps of:
   a) preparing a sample by combining a biological sample comprising the at least two target nucleic acid molecules and a known amount of at least two standard nucleic acids, wherein said at least two standard nucleic acids have a nucleotide sequence that is one base different than the respective target nucleic acid molecule sequence;
   b) amplifying the nucleic acids in the sample of step a);
   c) using a single base primer extension reaction at the site of differentiation between each of the standard and the target nucleic acid to produce at least two extended target-specific nucleic acids and at least two extended respective standard-specific nucleic acids;
   d) detecting the at least two extended target-specific nucleic acids and the at least two extended respective standard-specific nucleic acids in a single multiplex mass spectrometry assay to obtain a peak area for each of the extended target-specific and extended respective standard-specific nucleic acids; and
   e) quantifying the absolute amount of at least the two target nucleic acids by measuring a ratio of the peak area representing the extended target-specific nucleic acids and the extended respective standard-specific nucleic acids and calculating the absolute amount based on the amount of each standard initially added to the sample.

2. The method of claim 1, wherein the at least one of the two target nucleic acid molecules is from an infectious agent.

3. The method of claim 1, wherein the at least one of the two target nucleic acid molecules is an mRNA transcript.

* * * * *

SEQUENCE LISTING

```
<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 1
atggccacag ttgtatca                                                 18
```